(12) United States Patent
Wang et al.

(10) Patent No.: US 7,262,573 B2
(45) Date of Patent: Aug. 28, 2007

(54) MEDICAL TELE-ROBOTIC SYSTEM WITH A HEAD WORN DEVICE

(75) Inventors: Yulun Wang, Goleta, CA (US); Charles S. Jordan, Santa Barbara, CA (US); Keith Phillip Laby, Santa Barbara, CA (US); Jonathan Southard, Santa Barbara, CA (US)

(73) Assignee: InTouch Technologies, Inc., Goleta, CA (US)

( * ) Notice: Subject to any disclaimer, the term of this patent is extended or adjusted under 35 U.S.C. 154(b) by 0 days.

(21) Appl. No.: 10/781,150

(22) Filed: Feb. 17, 2004

(65) Prior Publication Data

US 2004/0174129 A1 Sep. 9, 2004

Related U.S. Application Data

(63) Continuation of application No. 60/452,695, filed on Mar. 6, 2003.

(51) Int. Cl.
*G02B 23/02* (2006.01)

(52) U.S. Cl. .................. 318/568.12; 318/568.24; 318/568.25; 700/264; 367/96; 348/143; 901/47; 382/153

(58) Field of Classification Search ........... 318/568.11, 318/568.12, 568.13, 100, 568.24, 568.25; 348/14.01, 14.07, 14.08, 563–570, 143; 345/660, 667; 700/264; 901/47; 367/96; 382/153
See application file for complete search history.

(56) References Cited

U.S. PATENT DOCUMENTS

| 3,821,995 | A | 7/1974 | Aghnides |
| 4,413,693 | A | 11/1983 | Derby |
| 4,471,354 | A | 9/1984 | Smith |
| 4,519,466 | A | 5/1985 | Shiraishi |
| 4,638,445 | A | 1/1987 | Mattaboni |
| 4,733,737 | A | 3/1988 | Falamak |
| 4,875,172 | A | 10/1989 | Kanayama |
| 4,977,971 | A | * | 12/1990 | Crane et al. .................. 180/8.3 |
| 5,073,749 | A | 12/1991 | Kanayama |

(Continued)

FOREIGN PATENT DOCUMENTS

CA 2289697 A1 11/1998

(Continued)

OTHER PUBLICATIONS

Baltus et al., "Towards Personal Service Robots for the Elderly", Computer Science and Robotoics.

(Continued)

*Primary Examiner*—Rita Leykin
(74) *Attorney, Agent, or Firm*—Ben J. Yorks; Irell & Manella LLP

(57) ABSTRACT

A robot system that includes a robot and a remote station. The remote station includes a head worn device worn on the head of a user. The head worn device senses movement of the user's head and generates corresponding input signals. The input signals are processed into robot movement commands and transmitted to the robot, typically through a broadband network. The robot movement commands move a camera of the robot. The camera movement tracks movement of the user's head so that the user can scan the visual field without having to generate separate input commands for the robot.

52 Claims, 10 Drawing Sheets

U.S. PATENT DOCUMENTS

| | | | |
|---|---|---|---|
| 5,130,794 A * | 7/1992 | Ritchey | 348/39 |
| 5,186,270 A | 2/1993 | West | |
| 5,305,427 A * | 4/1994 | Nagata | 700/259 |
| 5,341,242 A * | 8/1994 | Gilboa et al. | 359/631 |
| 5,341,854 A | 8/1994 | Zezulka et al. | |
| 5,374,879 A * | 12/1994 | Pin et al. | 318/139 |
| 5,419,008 A | 5/1995 | West | |
| 5,486,853 A * | 1/1996 | Baxter et al. | 348/222.1 |
| 5,510,832 A * | 4/1996 | Garcia | 348/56 |
| 5,544,649 A | 8/1996 | David et al. | |
| 5,572,229 A * | 11/1996 | Fisher | 345/8 |
| 5,630,566 A | 5/1997 | Case | |
| 5,636,218 A | 6/1997 | Ishikawa et al. | |
| 5,762,458 A | 6/1998 | Wang et al. | |
| 5,786,846 A * | 7/1998 | Hiroaki | 348/14.16 |
| 5,802,494 A | 9/1998 | Kuno | |
| 5,838,575 A | 11/1998 | Lion | |
| 5,857,534 A | 1/1999 | DeValult et al. | |
| 5,917,958 A * | 6/1999 | Nunally et al. | 382/276 |
| 5,959,423 A | 9/1999 | Nakanishi et al. | |
| 5,966,130 A | 10/1999 | Benman, Jr. | |
| 6,006,946 A | 12/1999 | Williams et al. | |
| 6,036,812 A | 3/2000 | Williams et al. | |
| 6,133,944 A * | 10/2000 | Braun et al. | 348/39 |
| 6,135,228 A | 10/2000 | Asada et al. | |
| 6,211,903 B1 * | 4/2001 | Bullister | 348/14.16 |
| 6,232,735 B1 * | 5/2001 | Baba et al. | 318/567 |
| 6,233,735 B1 * | 5/2001 | Ebihara | 725/101 |
| 6,259,806 B1 | 7/2001 | Green | |
| 6,292,713 B1 * | 9/2001 | Jouppi et al. | 700/245 |
| 6,304,050 B1 | 10/2001 | Skaar et al. | |
| 6,346,950 B1 | 2/2002 | Jouppi | |
| 6,369,847 B1 | 4/2002 | James et al. | |
| 6,430,471 B1 | 8/2002 | Kintou et al. | |
| 6,438,457 B1 | 8/2002 | Yokoo et al. | |
| 6,463,361 B1 | 10/2002 | Wang et al. | |
| 6,474,434 B1 | 11/2002 | Bech | |
| 6,491,701 B2 | 12/2002 | Tierney et al. | |
| 6,496,099 B2 | 12/2002 | Wang et al. | |
| 6,522,906 B1 | 2/2003 | Salisbury et al. | |
| 6,535,182 B2 * | 3/2003 | Stanton | 345/8 |
| 6,535,793 B2 * | 3/2003 | Allard | 700/259 |
| 6,543,899 B2 * | 4/2003 | Covannon et al. | 353/7 |
| 6,549,215 B2 * | 4/2003 | Jouppi | 345/660 |
| 6,587,750 B2 | 7/2003 | Gerbi et al. | |
| 6,594,552 B1 | 7/2003 | Nowlin et al. | |
| 6,684,129 B2 | 1/2004 | Salisbury et al. | |
| 6,799,065 B1 | 9/2004 | Niemeyer | |
| 6,804,656 B1 | 10/2004 | Rosenfeld et al. | |
| 6,839,612 B2 | 1/2005 | Sanchez et al. | |
| 6,852,107 B2 | 2/2005 | Wang et al. | |
| 6,879,879 B2 | 4/2005 | Jouppi et al. | |
| 6,995,664 B1 * | 2/2006 | Darling | 340/505 |
| 2001/0037163 A1 | 11/2001 | Allard | |
| 2001/0054071 A1 | 12/2001 | Loeb | |
| 2002/0027597 A1 | 3/2002 | Sachau | |
| 2002/0057279 A1 | 5/2002 | Jouppi | |
| 2002/0058929 A1 | 5/2002 | Green | |
| 2002/0063726 A1 | 5/2002 | Jouppi | |
| 2002/0120362 A1 | 8/2002 | Lathan et al. | |
| 2002/0130950 A1 | 9/2002 | James et al. | |
| 2002/0141595 A1 | 10/2002 | Jouppi | |
| 2002/0183894 A1 | 12/2002 | Wang et al. | |
| 2003/0050733 A1 | 3/2003 | Wang et al. | |
| 2003/0100892 A1 | 5/2003 | Morley et al. | |
| 2003/0114962 A1 | 6/2003 | Niemeyer | |
| 2003/0135203 A1 | 7/2003 | Wang et al. | |
| 2003/0144649 A1 | 7/2003 | Ghodoussi et al. | |
| 2003/0151658 A1 | 8/2003 | Smith | |
| 2003/0220541 A1 | 11/2003 | Salisbury et al. | |
| 2004/0019406 A1 | 1/2004 | Wang et al. | |

FOREIGN PATENT DOCUMENTS

| | | |
|---|---|---|
| EP | 0981905 B1 | 1/2002 |
| JP | 07257422 A | 10/1995 |
| JP | 2002-046088 | 2/2002 |
| JP | 2002305743 A | 10/2002 |

OTHER PUBLICATIONS

Bauer, Jeffrey C., "Service Robots in Health Care: The Evolution of Mechanical Solutions to Human Resource Problems", Jun. 2003.

Breslow, Michael J., MD et al., "Effect of a multiple-site intensive care unit telemedicine program on clinical and economic outcome: An alternative paradigm for intensivist staffing", Critical Care Med, Jan. 2004, vol. 32, No. 1, pp. 31-38.

Celi et al., "The eICU: It's not just telemedicine", Critical Care Medicine, vol. 29, No. 8 (Supplement), Aug. 2001.

CNN.com/Technology, Paging R.Robot: Machine helps doctors with patients, Sep. 30, 2003, Internet, 1-3.

Davies, "Robotics in Minimally Invasive Surgery", 1995, Internet, pp. 5/1-5/2.

Ellison et al., "Telerounding and Patient Satisfaction Following Surgery".

Goldman, Lea, "Machine Dreams", Entrepreneurs, Forbes, May 27, 2002.

Harmo et al., "Moving Eye—Interactive Telepresence Over Internet With a Ball Shaped Mobile Robot", 2000.

Hees, William P., "Communications Design for a Remote Presence Robot", Jan. 14, 2002.

Jouppi, et al., :Mutually-Immersive Audio Telepresence, Audio Engineering Society Convention Paper, presented at 113th Convention Oct. 2002.

Jouppi, Norman P., "First Steps Towards Mutually-Immersive Mobile Telepresence", 2002.

Kanehiro, Fumio et al., Virtual Humanoid Robot Platform to Develop Controllers of Real Humanoid Robots without Porting, 2001,IEEE, pp. 3217-3276.

Kaplan et al., "An Internet Accessible Telepresence".

Kuzuoka et al., "Can The GestureCam Be A Surrogate?".

Lim, Hun-ok et al., Control to Realize Human-like Walking of a Biped Humanoid Robot, IEE 2000, pp. 3271-3276.

Loeb, Gerald, "Virtual Visit: Improving Communication for Those Who Need It Most", 2001.

Mack, "Minimally invasive and robotic surgery", 2001, IEEE, pp. 568-572.

Magne Charge—Smart Power for Electric Vehicles, Internet, Jun. 27, 2002.

Martin, Anya, "Days Ahead", Assisted Living Today, vol. 9, Nov./Dec. 2002, pp. 19-22.

McCardle et al., "The challenge of utilizing new technology in design education", 2000 Internet, pp. 122-127.

Ojha, Anad, "An application of Virtual Reality in Rehabilitation", Jan. 1994, IEEE, pp. 4-6.

Paulos et al., "A World Wide Web Telerobotic Remote Environment Browser", http://vive.cs.berkeley.edu/capek, 1995.

Paulos, Eric John, "Personal Tele-Embodiment", 2001.

Paulos, et al., "Ubiquitous Tele-embodiment: Applications and Implications", International Journal of Human Computer Studies, Jun. 1997, vol. 46, No. 6, pp. 861-877.

Paulos, et al., "Designing Personal Tele-Embodiment", Presented at the IEEE International Conference on Robotics and Animation, Leuven, Belgium, May 20, 1998.

Pin et al., "A New Family of Omnidirectional and Holonomic Wheeled Platforms for Mobile Robots", IEEE, vol. 10, No. 4, Aug. 1994.

Roland Piquepaille's Technology Trends, How new technologies are modifying your way of life, 2003, Internet, pp. 1-2.

PYXIS HelpMate®, the Trackless Robotic Courier, Internet, 3 pgs.

"Remote Presence", p. 131-147.

Roy et al., "Towards Personal Service Robots for the Elderly", Internet, Mar. 7, 2002.

Stephenson, Gary, "Dr. Robot Tested at Hopkins", 2003, Internet, p. 1.

Stoianovici et al., "Robotic Tools for Minimally Invasive Urologic Surgery", Dec. 2002, Internet, 1-17.

Tendick et al., "Human-Machine Interfaces for Minimally Invasive Surgery", 1997, IEEE, pp. 1-6.

Thrun et al, "Probabilistic Algorithms and the Interactive Museum Tour-Guide Robot Minerva", 2000, Internet pp. 1-35.

Tzafestas, et al., "VR-based Teleoperation of a Mobile Robotic Assistant: Progress Report", 2000, Internet, pp. 1-23.

Urquhart, Kim, "InTouch's robotic Companion 'beams up' healthcare experts", Medical Device Daily, vol. 7, No. 39, Feb. 27, 2003, p. 1, 4.

Zorn, Benjamin G., "Ubiquitous Telepresence", http://www.cs.colorado.edu/~zorn/ut/vision/vision.html, Mar. 5, 1996.

\* cited by examiner

MEDICAL TELE-ROBOTIC SYSTEM WITH A HEAD WORN DEVICE

REFERENCE TO CROSS-RELATED APPLICATION

This application claims priority to Provisional Application No. 60/452,695 filed on Mar. 6, 2003.

BACKGROUND OF THE INVENTION

1. Field of the Invention

The subject matter disclosed generally relates to the field of robotics.

2. Background Information

There is a growing need to provide remote health care to patients that have a variety of ailments ranging from Alzheimers to stress disorders. To minimize costs it is desirable to provide home care for such patients. Home care typically requires a periodic visit by a health care provider such as a nurse or some type of assistant. Due to financial and/or staffing issues the health care provider may not be there when the patient needs some type of assistance. Additionally, existing staff must be continuously trained, which can create a burden on training personnel. It would be desirable to provide a system that would allow a health care provider to remotely care for a patient without being physically present.

Robots have been used in a variety of applications ranging from remote control of hazardous material to assisting in the performance of surgery. For example, U.S. Pat. No. 5,762,458 issued to Wang et al. discloses a system that allows a surgeon to perform minimally invasive medical procedures through the use of robotically controlled instruments. One of the robotic arms in the Wang system moves an endoscope that has a camera. The camera allows a surgeon to view a surgical area of a patient.

Tele-robots such as hazardous waste handlers and bomb detectors may contain a camera that allows the operator to view the remote site. Canadian Pat. No. 2289697 issued to Treviranus, et al. discloses a teleconferencing platform that has both a camera and a monitor. The platform includes mechanisms to both pivot and raise the camera and monitor. The Treviranus patent also discloses embodiments with a mobile platform, and different mechanisms to move the camera and the monitor.

There has been marketed a mobile robot introduced by InTouch-Health, Inc., the assignee of this application, under the trademark COMPANION. The COMPANION is controlled by a user at a remote station. The remote station may be a personal computer with a joystick that allows the user to remotely control the movement of the robot. Both the robot and remote station have cameras, monitors, speakers and microphones to allow for two-way video/audio communication.

To move the camera and scan the visual field of the robot the user must provide input movement at the remote station. For example, the user may have to move the joystick. Movement of the camera requires a set of input movements separate from movement of the robot. Having to multi-task between movement of the robot and movement of the robot camera increases the complexity of operating the system. It would be desirable to move the robot camera without having to specifically generate separate input commands.

BRIEF SUMMARY OF THE INVENTION

A robot system that includes a remote station and a robot. The remote station includes a head worn device that can generate input signals in response to movement of the device. The robot has a camera that moves in conjunction with movement of the head worn device and generated input signals.

DETAILED DESCRIPTION

Disclosed is a robot system that includes a robot and a remote station. The remote station includes a head worn device worn on the head of a user. The head worn device senses movement of the user's head and generates corresponding input signals. The input signals are processed into robot commands and transmitted to the robot, typically through a broadband network. The robot commands move a camera of the robot. The camera movement tracks movement of the user's head so that the user can scan the visual field without having to generate separate input commands for the robot. This simplifies usage of the system.

Figure 1:
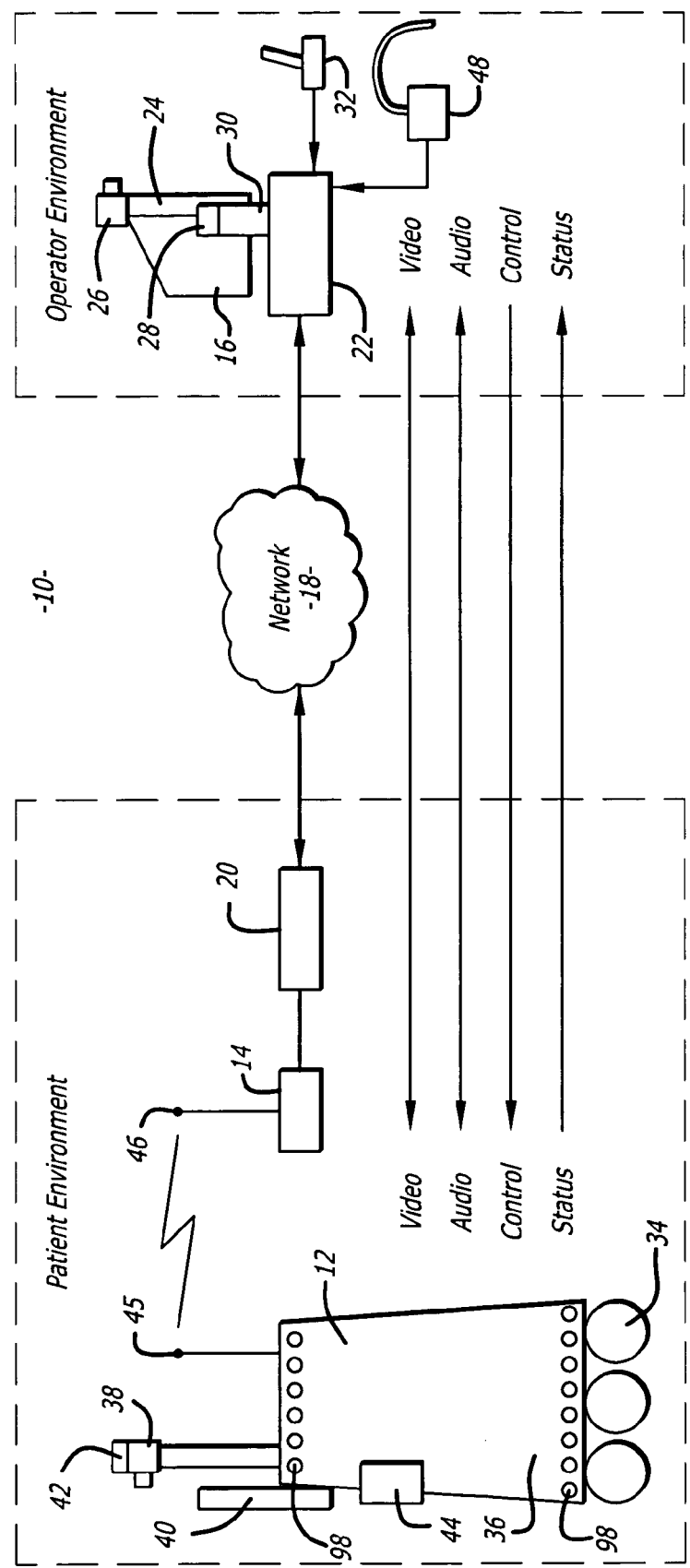
FIG. 1 is an illustration of a robotic system.

Referring to the drawings more particularly by reference numbers, FIG. 1 shows a robotic system 10. The robotic system 10 includes a robot 12, a base station 14 and a remote control station 16. The remote control station 16 may be coupled to the base station 14 through a network 18. By way of example, the network 18 may be either a packet switched network such as the Internet, or a circuit switched network such has a Public Switched Telephone Network (PSTN) or other broadband system. The base station 14 may be coupled to the network 18 by a modem 20 or other broadband network interface device.

The remote control station 16 may include a computer 22 that has a monitor 24, a camera 26, a microphone 28 and a speaker 30. The computer 22 may also contain an input device 32 such as a joystick or a mouse. The control station 16 is typically located in a place that is remote from the robot 12. Although only one remote control station 16 is shown, the system 10 may include a plurality of remote stations. In general any number of robots 12 may be controlled by any number of remote stations 16 or other robots 12. For example, one remote station 16 may be coupled to a plurality of robots 12, or one robot 12 may be coupled to a plurality of remote stations 16, or a plurality of robots 12.

Each robot 12 includes a movement platform 34 that is attached to a robot housing 36. Also attached to the robot housing 36 are a camera 38, a monitor 40, a microphone(s) 42 and a speaker(s) 44. The microphone 42 and speaker 30 may create a stereophonic sound. The robot 12 may also have an antenna 45 that is wirelessly coupled to an antenna 46 of the base station 14. The system 10 allows a user at the remote control station 16 to move the robot 12 through operation of the input device 32. The robot camera 38 is coupled to the remote monitor 24 so that a user at the remote station 16 can view a patient. Likewise, the robot monitor 40 is coupled to the remote camera 26 so that the patient can view the user. The microphones 28 and 42, and speakers 30 and 44, allow for audible communication between the patient and the user.

The remote station 16 includes a head worn device 48 that is coupled to the computer 22. The head worn device 48 is worn on the head of a user at the remote station 16. The device 48 includes motion sensors (not shown) to sense movement of the user's head and generate corresponding input signals that are provided to the computer 22. The sensors may be a level, gyroscopic or other type of motion sensing device.

The computer 22 processes the input signals from the head worn device 48 into robot commands that are transmitted to the robot 12. The robot commands cause corresponding movement of the robot camera 38. The camera movement 38 may track the movement of the user's head allowing the user to scan the visual field without generating separate input commands for the robot 12. For example, the user may move the robot 12 with the joystick 32 while scanning the visual field with the robot camera 38 by merely turning their head.

The microphone 28 may be integrated into the head worn device 48, or the device 48 may have a microphone separate from device 28. The computer 22 may contain a speech interface that can translate oral commands entered into the microphone. The oral commands may be translated into robot movement commands that are transmitted to the robot 12. The head worn device 48 may include a head up display that displays the video images captured by the robot camera 38 and/or information, such as graphics, provided by the computer 22.

The remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

Figure 2:
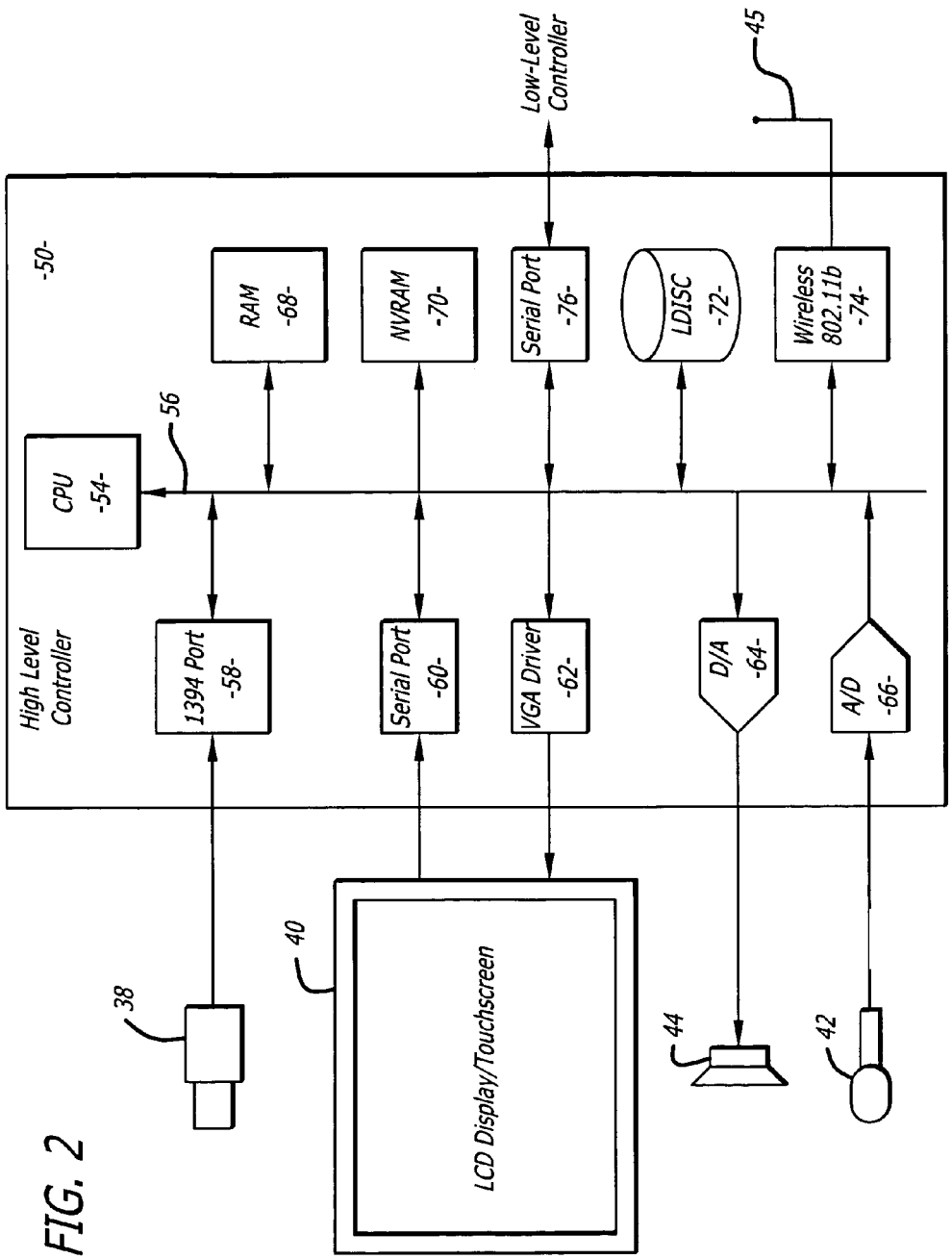
FIG. 2 is a schematic of an electrical system of a robot.
Figure 3:
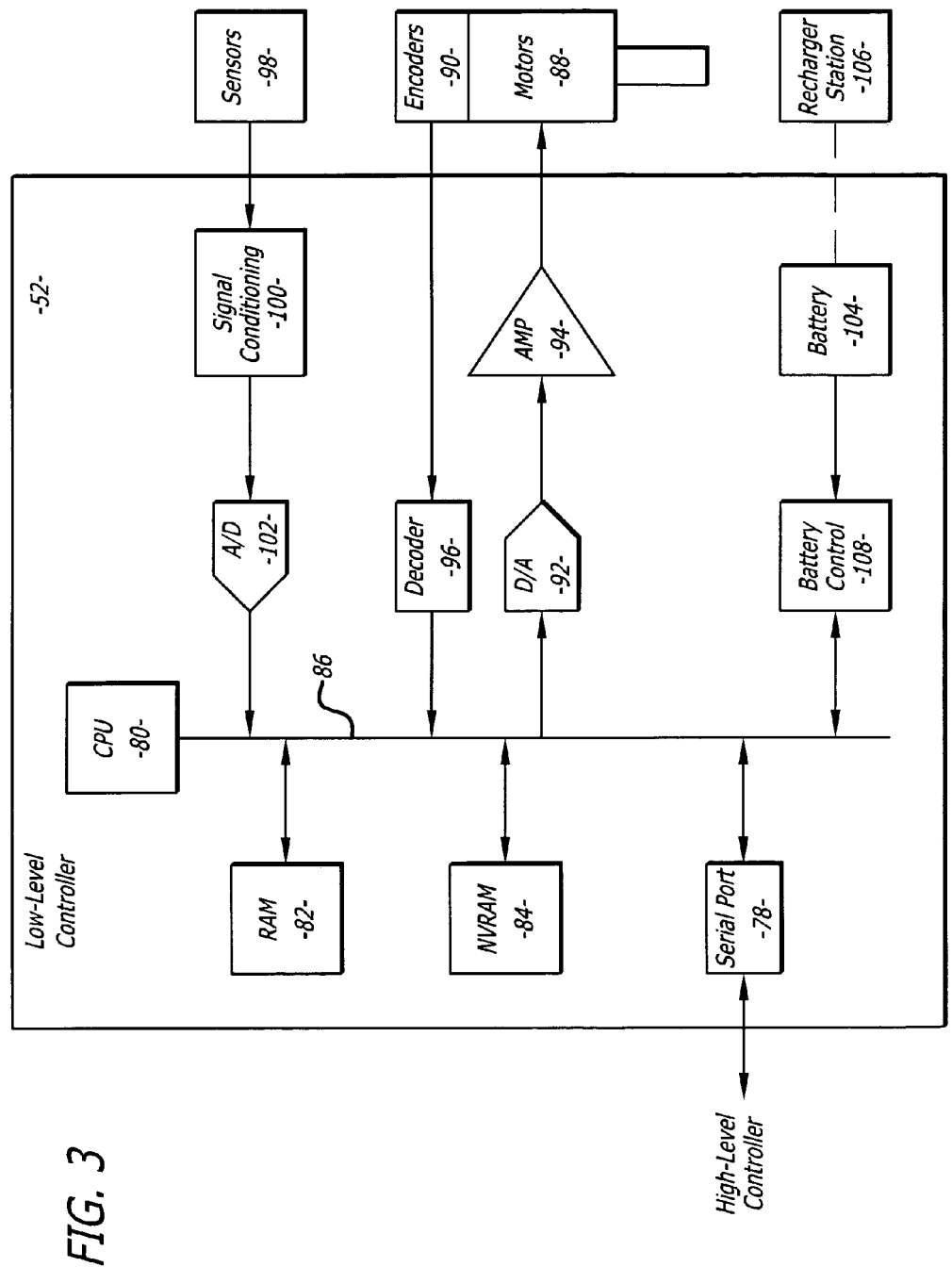
FIG. 3 is a further schematic of the electrical system of the robot.

FIGS. 2 and 3 show an embodiment of a robot 12. Each robot 12 may include a high level control system 50 and a low level control system 52. The high level control system 50 may include a processor 54 that is connected to a bus 56. The bus is coupled to the camera 38 by an input/output (I/O) port 58, and to the monitor 40 by a serial output port 60 and a VGA driver 62. The monitor 40 may include a touchscreen function that allows the patient to enter input by touching the monitor screen.

The speaker 44 is coupled to the bus 56 by a digital to analog converter 64. The microphone 42 is coupled to the bus 56 by an analog to digital converter 66. The input device 48 is coupled to the bus by an analog to digital converter 67. Movement of the input device 48 is converted to digital bit string that are processed by controller 50 and transmitted to the base station 14, through the network 18 and to another robot 12. The high level controller 50 may also contain random access memory (RAM) device 68, a non-volatile RAM device 70 and a mass storage device 72 that are all coupled to the bus 62. The mass storage device 72 may contain medical files of the patient that can be accessed by the user at the remote control station 16. For example, the mass storage device 72 may contain a picture of the patient. The user, particularly a health care provider, can recall the old picture and make a side by side comparison on the monitor 24 with a present video image of the patient provided by the camera 38. The robot antennae 45 may be coupled to a wireless transceiver 74. By way of example, the transceiver 74 may transmit and receive information in accordance with IEEE 802.11b.

The controller 54 may operate with a LINUX OS operating system. The controller 54 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 50 operates to control communication between the robot 12 and the remote control station 16.

The high level controller 50 may be linked to the low level controller 52 by serial ports 76 and 78. The low level controller 52 includes a processor 80 that is coupled to a RAM device 82 and non-volatile RAM device 84 by a bus 86. Each robot 12 contains a plurality of motors 88 and motor encoders 90. The encoders 90 provide feedback information regarding the output of the motors 88. The motors 88 can be coupled to the bus 86 by a digital to analog converter 92 and a driver amplifier 94. The encoders 90 can be coupled to the bus 86 by a decoder 96. Each robot 12 also has a number of proximity sensors 98 (see also FIG. 1). The position sensors 98 can be coupled to the bus 86 by a signal conditioning circuit 100 and an analog to digital converter 102.

The low level controller 52 runs software routines that mechanically actuate the robot 12. For example, the low level controller 52 provides instructions to actuate the movement platform to move the robot 12. The low level controller 52 may receive movement instructions from the high level controller 50. The movement instructions may be received as movement commands from the remote control station or another robot. Although two controllers are shown, it is to be understood that each robot 12 may have one controller, or more than two controllers, controlling the high and low level functions.

The various electrical devices of each robot 12 may be powered by a battery(ies) 104. The battery 104 may be recharged by a battery recharger station 106 (see also FIG. 1). The low level controller 52 may include a battery control circuit 108 that senses the power level of the battery 104. The low level controller 52 can sense when the power falls below a threshold and then send a message to the high level controller 50. The high level controller 50 may include a power management software routine that causes the robot 12 to move so that the battery 104 is coupled to the recharger 106 when the battery power falls below a threshold value. Alternatively, the user can direct the robot 12 to the battery recharger 106. Additionally, the battery 104 may be replaced or the robot 12 may be coupled to a wall power outlet by an electrical cord (not shown).

Figure 4:
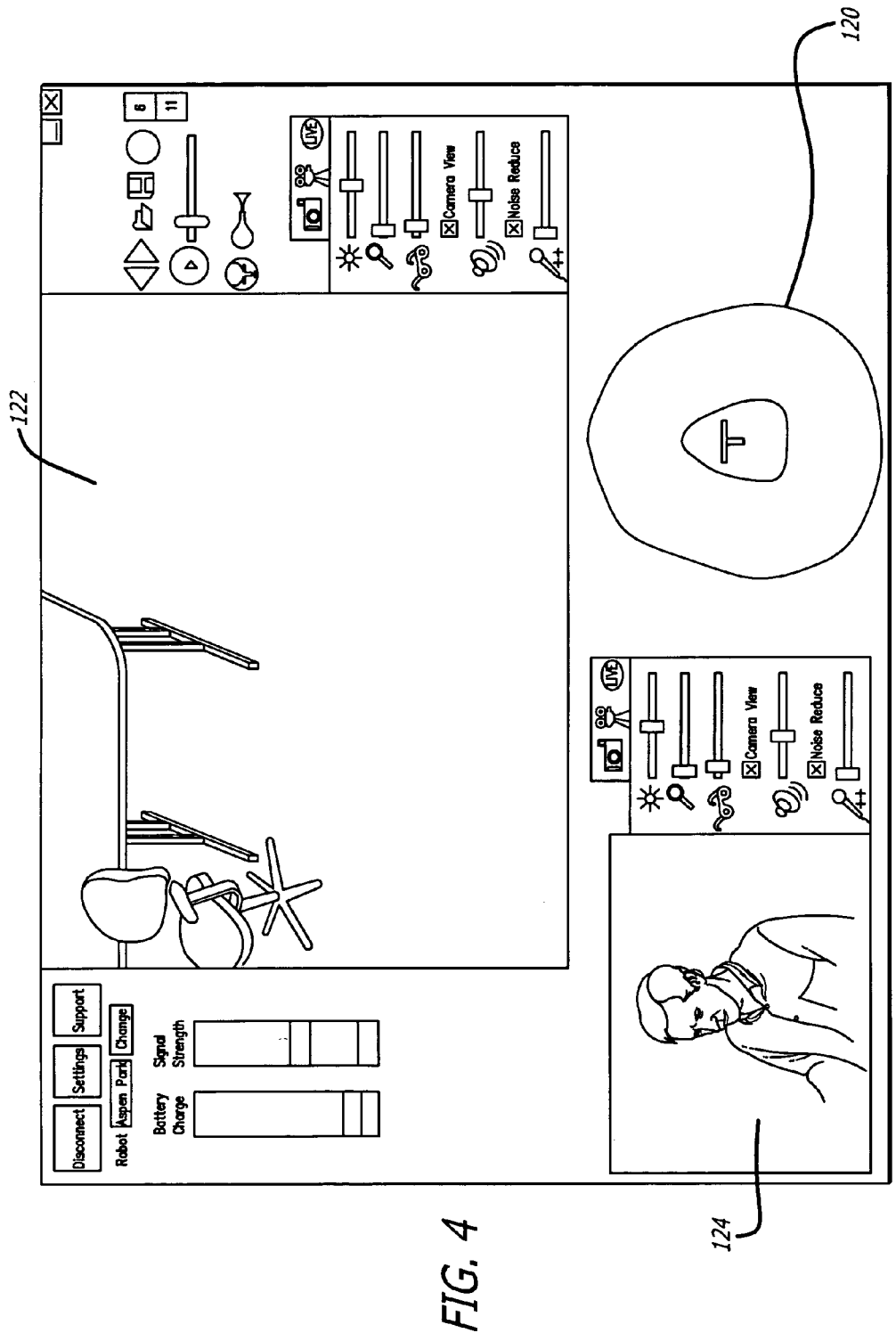
FIG. 4 is a graphical user interface of a remote station.

FIG. 4 shows a graphical user interface ("GUI") 120 that can be displayed at the remote station 16. The GUI 120 may include a robot view field 122 that displays a video image provided by the camera of the robot. The GUI 120 may also include a station view field 124 that displays a video image provided by the camera of the remote station 16. The GUI 120 may part of an application program stored and operated by the computer 22 of the remote station 16.

Figure 5:
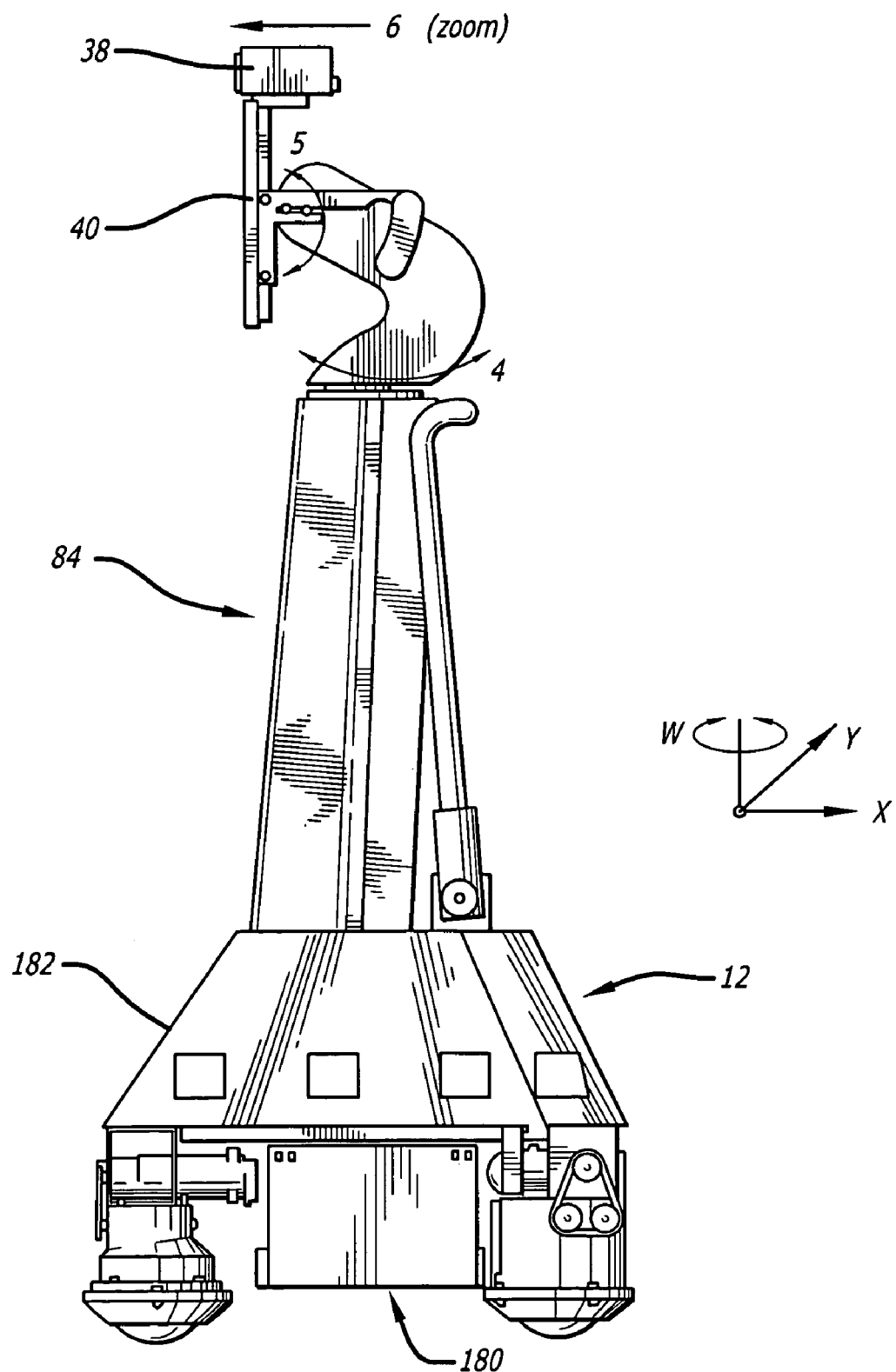
FIG. 5 is side view of a robot.

FIG. 5 shows an embodiment of a robot 12. Each robot 12 may include a holonomic platform 180 that is attached to a robot housing 182. The holonomic platform 180 provides three degrees of freedom to allow the robot 12 to move in any direction.

Each robot 12 may have an pedestal assembly 184 that supports the camera 38 and the monitor 40. The pedestal assembly 184 may have two degrees of freedom so that the camera 26 and monitor 24 can be swiveled and pivoted as indicated by the arrows.

Figure 6:
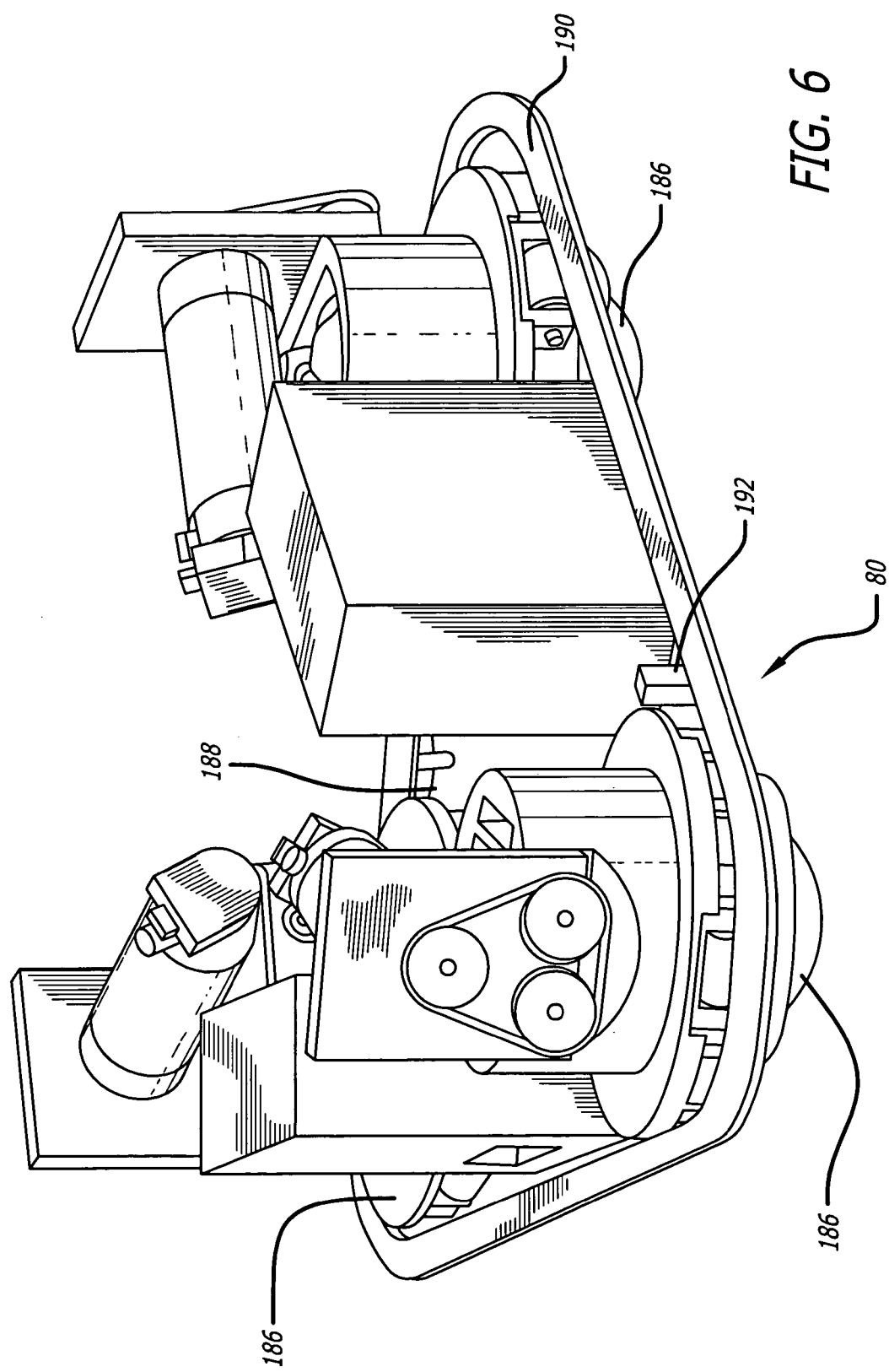
FIG. 6 is a top perspective view of a holonomic platform of the robot.

As shown in FIG. 6 the holonomic platform 180 may include three roller assemblies 186 that are mounted to a base plate 188. The roller assemblies 186 allow for movement in any direction along a surface.

The robot housing 182 may include a bumper 190. The bumper 190 may be coupled to optical position sensors 192 that detect when the bumper 190 has engaged an object. After engagement with the object the robot can determine the direction of contact and prevent further movement into the object.

Figure 7:
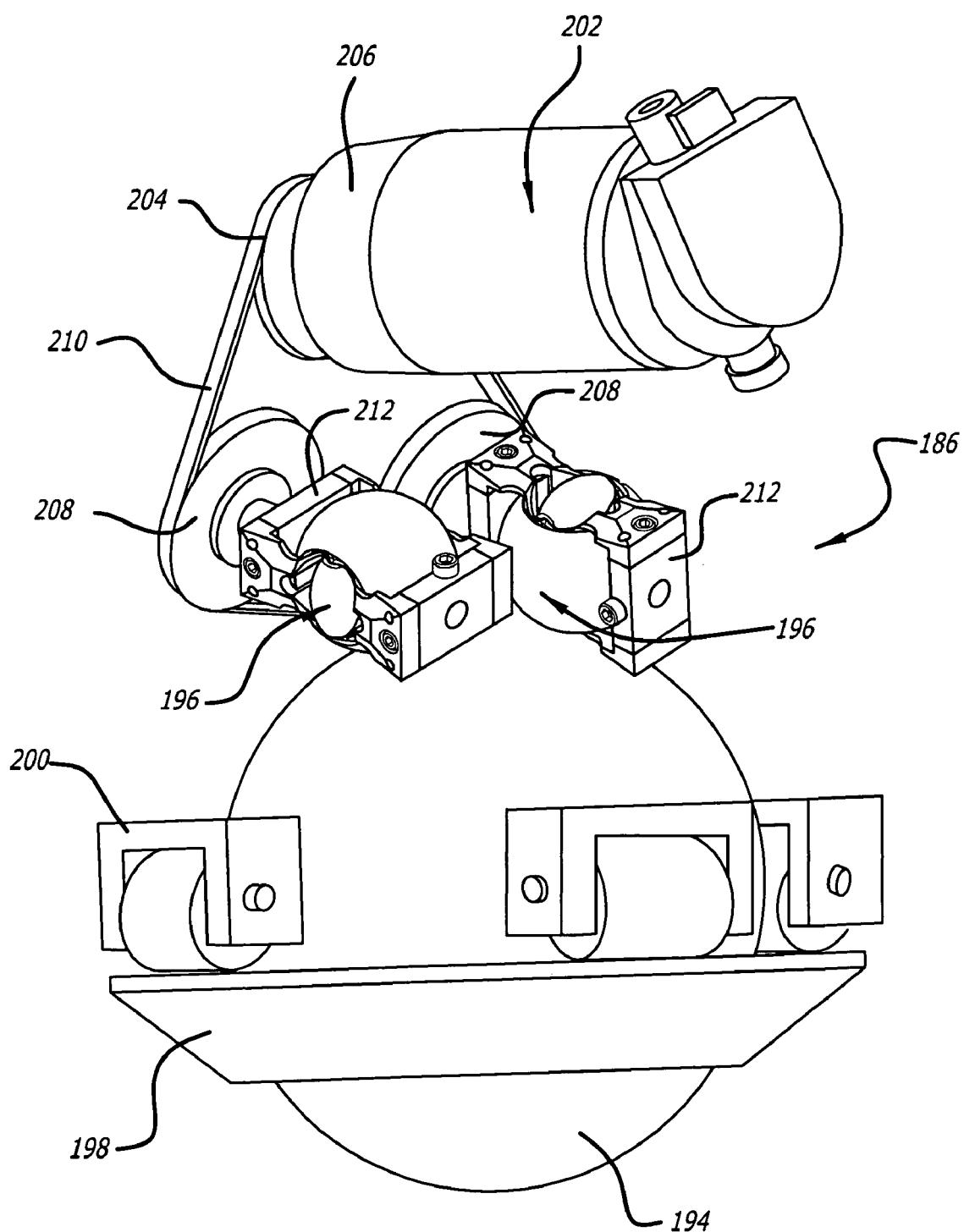
FIG. 7 is a side perspective view of a roller assembly of the holonomic platform.

FIG. 7 shows an embodiment of a roller assembly 186. Each assembly 186 may include a drive ball 194 that is driven by a pair of transmission rollers 196. The assembly 186 includes a retainer ring 198 and a plurality of bushings 200 that allow the ball 194 to rotate in an x and y direction but prevents movement in a z direction.

The transmission rollers 196 are coupled to a motor assembly 202. The assembly 202 corresponds to the motor 88 shown in FIG. 3. The motor assembly 202 includes an output pulley 204 attached to a motor 206. The output pulley 204 is coupled to a pair of ball pulleys 208 by a drive belt 210. The ball pulleys 208 are each attached to a transmission bracket 212. The transmission rollers 196 are attached to the transmission brackets 212.

Rotation of the output pulley 204 rotates the ball pulleys 208. Rotation of the ball pulleys 208 causes the transmission rollers 196 to rotate and spin the ball 194 through frictional forces. Spinning the ball 194 will move the robot 12. The transmission rollers 196 are constructed to always be in contact with the drive ball 194. The brackets 212 allow the transmission rollers 196 to freely spin in a direction orthogonal to the driven direction when one of the other roller assemblies 186 is driving and moving the robot 12.

Figure 8:
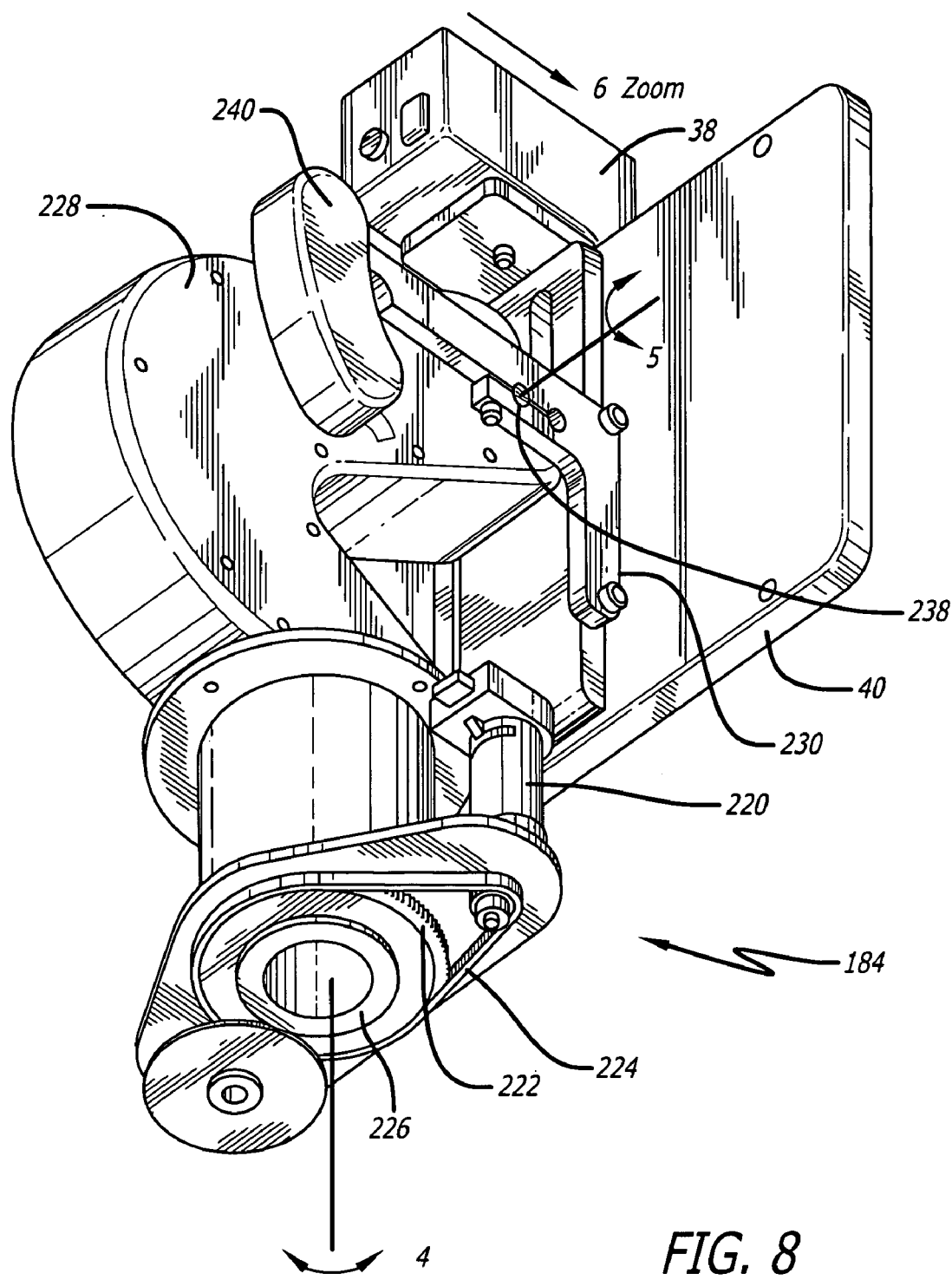
FIG. 8 is a bottom perspective view showing a pedestal assembly of the robot.

As shown in FIG. 8, the pedestal assembly 184 may include a motor 220 that is coupled to a gear 222 by a belt 224. The gear 222 is attached to a sleeve 226 that can rotate. The sleeve 226 is coupled to an arm 228 that is coupled to the camera 38 and monitor 40 by a bracket 230. Activation of the motor 220 rotates the gear 222 and causes the camera 38 and monitor 40 to swivel (see also FIG. 4) as indicated by the arrows 4.

Figure 9:
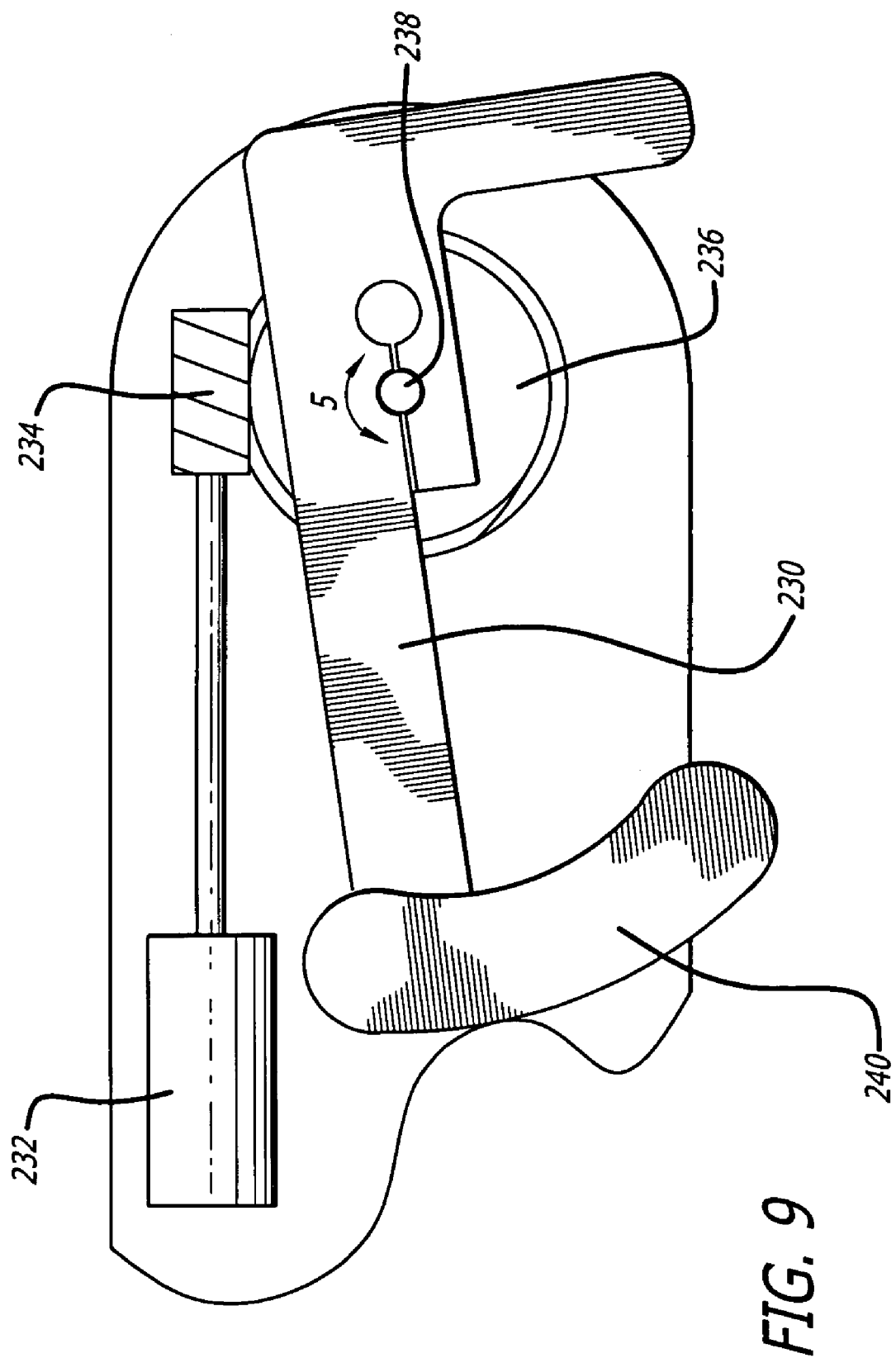
FIG. 9 is a sectional view showing an actuator of the pedestal assembly.

As shown in FIG. 9, the assembly 184 may further include a tilt motor 232 within the arm 238 that can cause the monitor 40 and camera 38 to pivot as indicated by the arrows 5. The tilt motor 232 may rotate a worm 234 that rotates a worm gear 236. The pin 238 is rigidly attached to both the worm gear 236 and the bracket 230 so that rotation of the gear 236 pivots the camera 38 and the monitor 40. The camera 38 may also include a zoom feature to provide yet another degree of freedom for the operator.

In operation, each robot 12 may be placed in a home or a facility where one or more patients are to be monitored and/or assisted. The facility may be a hospital or a residential care facility. By way of example, the robot 12 may be placed in a home where a health care provider may monitor and/or assist the patient. Likewise, a friend or family member may communicate with the patient. The cameras and monitors at both the robot and remote control station allow for teleconferencing between the patient and the person at the remote station, or another robot.

Each robot 12 can be maneuvered through the home or facility by manipulating the input device 32 at the remote station 16.

Each robot 10 may be controlled by a number of different users at the remote station(s) 16. To accommodate for this each robot may have an arbitration system. The arbitration system may be integrated into the operating system of the robot 12. For example, the arbitration technique may be embedded into the operating system of the high-level controller 50.

By way of example, the users may be divided into classes that include the robot itself, a local user, a caregiver, a doctor, a family member, or a service provider. These users may provide input from either a remote station or another robot. The robot may override input commands that conflict with robot operation. For example, if the robot runs into a wall, the system may ignore all additional commands to continue in the direction of the wall. A local user is a person who is physically present with the robot. The robot could have an input device that allows local operation. The same input device may also control a different robot.

A caregiver is someone who remotely monitors the patient. A doctor is a medical professional who can remotely control the robot and also access medical files contained in the robot memory. The family and service users remotely access the robot. The service user may service the system such as by upgrading software, or setting operational parameters.

Message packets may be transmitted between a robot 12 and a remote station 16 or between robots 12. The packets provide commands and feedback. Each packet may have multiple fields. By way of example, a packet may include an ID field a forward speed field, an angular speed field, a stop field, a bumper field, a sensor range field, a configuration field, a text field and a debug field.

The identification of remote users can be set in an ID field of the information that is transmitted from the remote control station 16 to the robot 12. For example, a user may enter a user ID into a setup table in the application software run by the remote control station 16. The user ID is then sent with each message transmitted to the robot.

Each robot 12 may operate in different modes; an exclusive mode, a sharing mode, or a remote station mode. In the exclusive mode only one user has access control of the robot. The exclusive mode may have a priority assigned to each type of user. By way of example, the priority may be in order of local, doctor, caregiver, family and then service user. In the sharing mode two or more users may share access with the robot. For example, a caregiver may have access to the robot, the caregiver may then enter the sharing mode to allow a doctor to also access the robot. Both the caregiver and the doctor can conduct a simultaneous teleconference with the patient.

The arbitration scheme may have one of four mechanisms; notification, timeouts, queue and call back. The notification mechanism may inform either a present user or a requesting user that another user has, or wants, access to the robot. The timeout mechanism gives certain types of users a prescribed amount of time to finish access to the robot. The queue mechanism is an orderly waiting list for access to the robot. The call back mechanism informs a user that the robot can be accessed. By way of example, a family user may receive an e-mail message that the robot is free for usage. Tables 1 and 2, show how the mechanisms resolve access request from the various users.

TABLE I

| User | Access Control | Medical Record | Command Override | Software/Debug Access | Set Priority |
|---|---|---|---|---|---|
| Robot | No | No | Yes (1) | No | No |
| Local | No | No | Yes (2) | No | No |
| Caregiver | Yes | Yes | Yes (3) | No | No |
| Doctor | No | Yes | No | No | No |
| Family | No | No | No | No | No |
| Service | Yes | No | Yes | Yes | Yes |

TABLE II

| | | Requesting User | | | | |
|---|---|---|---|---|---|---|
| | | Local | Caregiver | Doctor | Family | Service |
| Current User | Local | Not Allowed | Warn current user of pending user<br>Notify requesting user that system is in use<br>Set timeout | Warn current user of pending user<br>Notify requesting user that system is in use<br>Set timeout = 5 m | Warn current user of pending user<br>Notify requesting user that system is in use<br>Set timeout = 5 m<br>Call back | Warn current user of pending user<br>Notify requesting user that system is in use<br>No timeout<br>Call back |
| | Caregiver | Warn current user of pending user.<br>Notify requesting user that system is in use.<br>Release control | Not Allowed | Warn current user of pending user<br>Notify requesting user that system is in use<br>Set timeout = 5 m<br>Queue or callback | Warn current user of pending user<br>Notify requesting user that system is in use<br>Set timeout = 5 m | Warn current user of pending user<br>Notify requesting user that system is in use<br>No timeout<br>Callback |
| | Doctor | Warn current user of pending user<br>Notify requesting user that system is in use<br>Release control | Warn current user of pending user<br>Notify requesting user that system is in use<br>Set timeout = 5 m | Warn current user of pending user<br>Notify requesting user that system is in use<br>No timeout<br>Callback | Notify requesting user that system is in use<br>No timeout<br>Queue or callback | Warn current user of pending user<br>Notify requesting user that system is in use<br>No timeout<br>Callback |
| | Family | Warn current user of pending user<br>Notify requesting user that system is in use<br>Release Control | Notify requesting user that system is in use<br>No timeout<br>Put in queue or callback | Warn current user of pending user<br>Notify requesting user that system is in use<br>Set timeout = 1 m | Warn current user of pending user<br>Notify requesting user that system is in use<br>Set timeout = 5 m<br>Queue or callback | Warn current user of pending user<br>Notify requesting user that system is in use<br>No timeout<br>Callback |
| | Service | Warn current user of pending user<br>Notify requesting user that system is in use<br>No timeout | Notify requesting user that system is in use<br>No timeout<br>Callback | Warn current user of request<br>Notify requesting user that system is in use<br>No timeout<br>Callback | Warn current user of pending user<br>Notify requesting user that system is in use<br>No timeout<br>Queue or callback | Not Allowed |

The information transmitted between the station 16 and the robot 12 may be encrypted. Additionally, the user may have to enter a password to enter the system 10. A selected robot is then given an electronic key by the station 16 or another robot 12. The robot 12 validates the key and returns another key to the station 16. The keys are used to encrypt information transmitted in the session.

In the remote station mode, a robot can be used to control another robot. An operator can move the joystick 48 to move the other robot like the joystick 32 of the remote station is used to control a robot. The operator can select a robot of choice through an input device of the master robot. By way of example, the input device may be a touch pad graphical user interface provided by the monitor 40.

Figure 10:
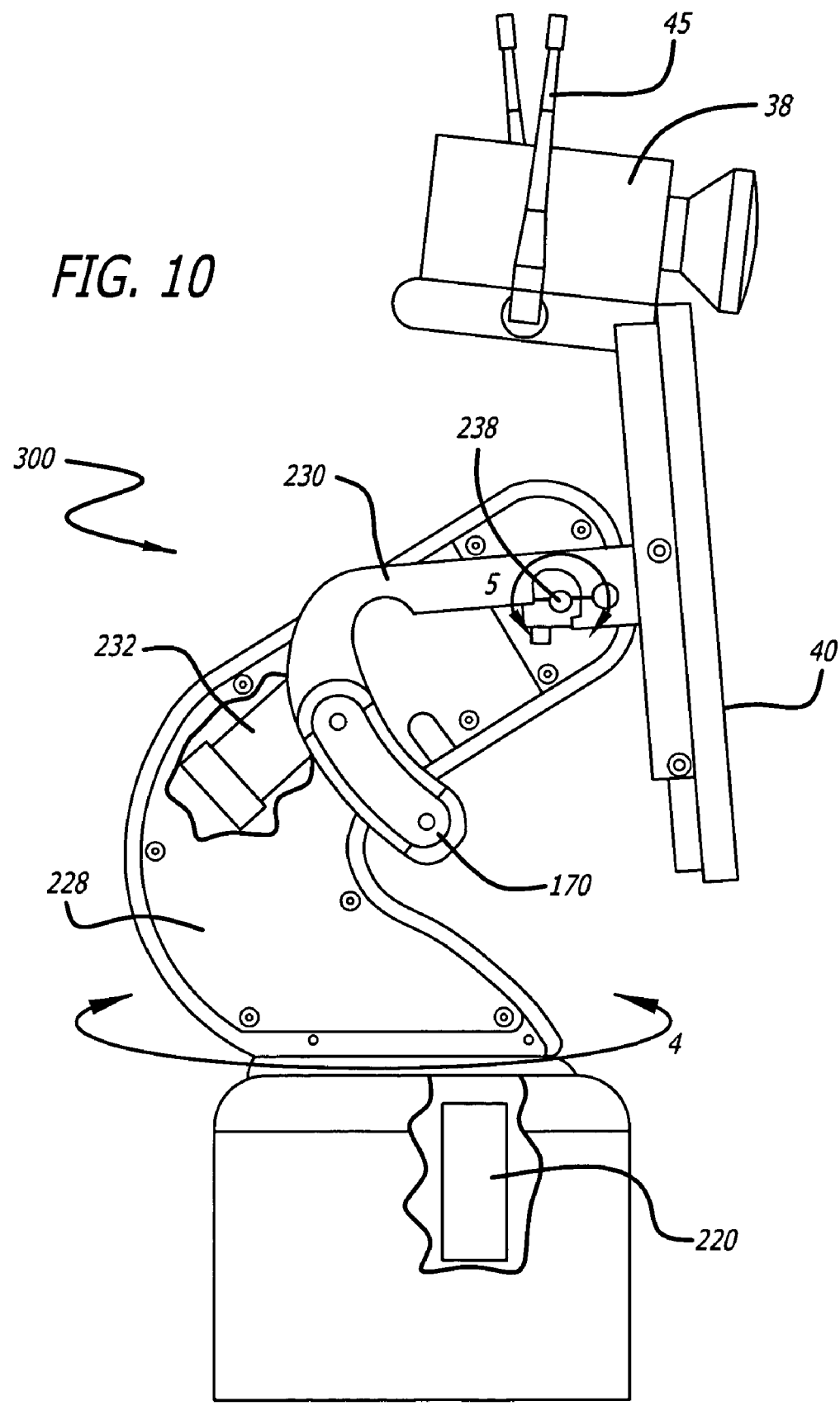
FIG. 10 is a side view of a robot head.

FIG. 10 shows a robot head 300 that can both pivot and spin the camera 38 and the monitor 40. The robot head 300 can be similar to the robot 12 but without the platform 180. The robot head 300 may have the same mechanisms and parts to both pivot the camera 38 and monitor 40 about the pivot axis 4, and spin the camera 38 and monitor 40 about the spin axis 5. The pivot axis may intersect the spin axis. Having a robot head 300 that both pivots and spins provides a wide viewing area. The robot head 300 may be accessed in the same manner as the mobile robot 12.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A robot system, comprising:
   a remote station that has a camera that captures a remote station image;
   a mobile robot that is controlled by said remote station and has a monitor that displays the remote station image, and a camera that captures a robot image, said monitor and said camera move together in at least two degrees of freedom; and,
   a head worn device, said head worn device generates input signals in response to movement of said head worn device, said robot camera moves in conjunction with the movement of said head worn device, said head worn device displays said robot images.

2. The system of claim 1, wherein said mobile robot includes a holonomic mobile platform.

3. The system of claim 1, wherein said head worn device displays graphics.

4. The system of claim 1, wherein said head worn device includes a microphone.

5. The system of claim 4, wherein said remote station includes a speech interface that interprets robot commands entered through said microphone.

6. A robot system, comprising:
a remote station with a camera that captures a remote station image;
a mobile robot that is controlled by said remote station and has a monitor that displays the remote station image and a camera captures a robot image, said monitor and said camera move together in at least two degrees of freedom; and,
head worn means for moving said robot camera in conjunction with movement of a user's head and displaying the robot images.

7. The system of claim 6, wherein said mobile robot includes a holonomic mobile platform.

8. The system of claim 6, wherein said head worn device means displays graphics.

9. The system of claim 6, wherein said head worn means includes a microphone.

10. The system of claim 9, wherein said remote station includes a speech interface that interprets robot commands entered through said microphone.

11. A method for moving a camera of a robot, comprising:
moving a head worn device;
generating input signals that correspond to the movement of the head worn device;
processing the input signals into a robot command;
transmitting the robot command to a robot;
moving together a monitor and a camera of the robot in response to the robot command in at least two degrees of freedom;
capturing a robot image with the robot camera;
capturing a remote station image with a remote station camera;
displaying the robot image with the head worn device;
displaying the remote station image on the monitor of the robot; and,
moving the robot across a surface.

12. The method of claim 11, further comprising transmitting video images between the robot and a remote station.

13. The method of claim 11, further comprising entering a robot input command into a microphone of the head worn device and processing the robot input command into a robot movement command, transmitting the robot movement command to the robot, and moving the robot.

14. A robot system, comprising:
a broadband network;
a remote station that is coupled to said broadband network and has a camera that captures a remote station image;
a mobile robot that is controlled by said remote station and coupled to said broadband network and has a monitor that displays the remote station image, and a camera that captures a robot image, said monitor and said camera move together in at least two degrees of freedom; and,
a head worn device, said head worn device generates input signals in response to movement of said head worn device, said robot camera moves in conjunction with the movement of said head worn device, said head worn device displays said robot images.

15. The system of claim 14, wherein said mobile robot includes a holonomic mobile platform.

16. The system of claim 14, wherein said head worn device displays graphics.

17. The system of claim 14, wherein said head worn device includes a microphone.

18. The system of claim 17, wherein said remote station includes a speech interface that interprets robot commands entered through said microphone.

19. A robot system, comprising:
a broadband network;
a remote station that is coupled to said broadband network, said remote station has a camera that captures a remote station image;
a mobile robot that is controlled by said remote station and is coupled to said broadband network and has a monitor that displays the remote station image, and a camera that captures a robot image, said monitor and said camera move together in at least two degrees of freedom; and,
a head worn device means for moving said robot camera in conjunction with movement of a user's head and displaying the robot images.

20. The system of claim 19, wherein said mobile robot includes a holonomic mobile platform.

21. The system of claim 19, wherein said head worn means displays graphics.

22. The system of claim 19, wherein said head worn means includes a microphone.

23. The system of claim 22, wherein said remote station includes a speech interface that interprets robot commands entered through said microphone.

24. A method for moving a camera of a robot, comprising:
moving a head worn device;
generating input signals that correspond to the movement of the head worn device;
processing the input signals into a robot command;
transmitting the robot command to a robot through a broadband network;
moving together a monitor and a camera of the robot in response to the robot command in at least two degrees of freedom;
capturing a robot image with the robot camera;
capturing a remote station image with a remote station camera;
displaying the robot image with the head worn device;
displaying the remote station image on the monitor of the robot; and,
moving the robot across a surface.

25. The method of claim 24, further comprising transmitting video images between the robot and a remote station.

26. The method of claim 25, further comprising entering a robot input command into a microphone of the head worn device and processing the robot input command into a robot movement command, transmitting the robot movement command to the robot, and moving the robot.

27. A robot system, comprising:
a remote station that has a camera that captures a remote station image;
a mobile robot that is controlled by said remote station and has a single monitor that swivels and displays the remote station image, and a camera that captures a robot image; and,
a head worn device, said head worn device generates input signals in response to movement of said head worn device, said robot camera moves in conjunction with the movement of said head worn device, said head worn device displays said robot images.

28. The system of claim 27, wherein said mobile robot includes a holonomic mobile platform.

29. The system of claim 27, wherein said head worn device displays graphics.

30. The system of claim 27, wherein said head worn device includes a microphone.

31. The system of claim 30, wherein said remote station includes a speech interface that interprets robot commands entered through said microphone.

32. A robot system, comprising:
a remote station with a camera that captures a remote station image;
a mobile robot that is controlled by said remote station and has a single monitor that swivels and displays the remote station image and a camera that captures a robot image; and,
head worn means for moving said robot camera in conjunction with movement of a user's head and displaying the robot images.

33. The system of claim 32, wherein said mobile robot includes a holonomic mobile platform.

34. The system of claim 32, wherein said head worn device means displays graphics.

35. The system of claim 32, wherein said head worn means includes a microphone.

36. The system of claim 35, wherein said remote station includes a speech interface that interprets robot commands entered through said microphone.

37. A method for moving a camera of a robot, comprising:
moving a head worn device;
generating input signals that correspond to the movement of the head worn device;
processing the input signals into a robot command;
transmitting the robot command to a robot;
swiveling a monitor and a camera of the robot in response to the robot command;
capturing a robot image with the robot camera;
capturing a remote station image with a remote station camera;
displaying the robot image with the head worn device;
displaying the remote station image on the monitor of the robot; and,
moving the robot across a surface.

38. The method of claim 37, further comprising transmitting video images between the robot and a remote station.

39. The method of claim 37, further comprising entering a robot input command into a microphone of the head worn device and processing the robot input command into a robot movement command, transmitting the robot movement command to the robot, and moving the robot.

40. A robot system, comprising:
a broadband network;
a remote station that is coupled to said broadband network and has a camera that captures a remote station image;
a mobile robot that is controlled by said remote station and coupled to said broadband network and has a single monitor that swivels and displays the remote station image, and a camera that captures a robot image; and,
a head worn device, said head worn device generates input signals in response to movement of said head worn device, said robot camera moves in conjunction with the movement of said head worn device, said head worn device displays said robot images.

41. The system of claim 14, wherein said mobile robot includes a holonomic mobile platform.

42. The system of claim 14, wherein said head worn device displays graphics.

43. The system of claim 14, wherein said head worn device includes a microphone.

44. The system of claim 17, wherein said remote station includes a speech interface that interprets robot commands entered through said microphone.

45. A robot system, comprising:
a broadband network;
a remote station that is coupled to said broadband network, said remote station has a camera that captures a remote station image;
a mobile robot that is controlled by said remote station and is coupled to said broadband network and has a single monitor that swivels and displays the remote station image, and a camera that captures a robot image; and,
a head worn device means for moving said robot camera in conjunction with movement of a user's head and displaying the robot images.

46. The system of claim 45, wherein said mobile robot includes a holonomic mobile platform.

47. The system of claim 45, wherein said head worn means displays graphics.

48. The system of claim 45, wherein said head worn means includes a microphone.

49. The system of claim 48, wherein said remote station includes a speech interface that interprets robot commands entered through said microphone.

50. A method for moving a camera of a robot, comprising:
moving a head worn device;
generating input signals that correspond to the movement of the head worn device;
processing the input signals into a robot command;
transmitting the robot command to a robot through a broadband network;
swiveling a monitor and a camera of the robot in response to the robot command;
capturing a robot image with the robot camera;
capturing a remote station image with a remote station camera;
displaying the robot image with the head worn device;
displaying the remote station image on the monitor of the robot; and,
moving the robot across a surface.

51. The method of claim 50, further comprising transmitting video images between the robot and a remote station.

52. The method of claim 50, further comprising entering a robot input command into a microphone of the head worn device and processing the robot input command into a robot movement command, transmitting the robot movement command to the robot, and moving the robot.

* * * * *